US005777734A

United States Patent [19]
Flower et al.

[11] Patent Number: 5,777,734
[45] Date of Patent: Jul. 7, 1998

[54] METHOD AND APPARATUS FOR CALIBRATING A PARTICLE EMISSIONS MONITOR

[75] Inventors: William L. Flower, Livermore; Ronald F. Renzi, Tracy, both of Calif.

[73] Assignee: Sandia Corporation, Livermore, Calif.

[21] Appl. No.: 585,341

[22] Filed: Jan. 11, 1996

Related U.S. Application Data

[63] Continuation-in-part of Ser. No. 228,974, Apr. 15, 1994.
[51] Int. Cl.$^6$ .................................................. G01N 21/00
[52] U.S. Cl. ................................... 356/341; 250/252.1 R
[58] Field of Search .......................... 356/36, 319, 318, 356/313, 316, 341, 417, 436, 437, 438, 439, 441, 442, 433, 434, 435; 250/288, 252.1 R

[56] References Cited

U.S. PATENT DOCUMENTS 5,369,035  11/1994  Eastgate et al. .
5,526,110   6/1996  Braymen ................................. 356/316

FOREIGN PATENT DOCUMENTS

WO9307453  4/1993  WIPO ..................................... 356/319

*Primary Examiner*—K. Hantis
*Attorney, Agent, or Firm*—Timothy Stanley

[57] ABSTRACT

The instant invention discloses method and apparatus for calibrating particulate emissions monitors, in particular, and sampling probes, in general, without removing the instrument from the system being monitored. A source of one or more specific metals in aerosol (either solid or liquid) or vapor form is housed in the instrument. The calibration operation is initiated by moving a focusing lens, used to focus a light beam onto an analysis location and collect the output light response, from an operating position to a calibration position such that the focal point of the focusing lens is now within a calibration stream issuing from a calibration source. The output light response from the calibration stream can be compared to that derived from an analysis location in the operating position to more accurately monitor emissions within the emissions flow stream.

8 Claims, 4 Drawing Sheets

METHOD AND APPARATUS FOR CALIBRATING A PARTICLE EMISSIONS MONITOR

This application is a continuation-in-part of copending application Ser. No. 08/228.974 filed on Apr. 15, 1994 and entitled A DEVICE FOR CONITNUOUS MONITORING OF PARTICULATE EMISSIONS.

STATEMENT OF GOVERNMENT INTEREST

The government has rights in this invention pursuant to contract no. DE - AC04 - 94AL85000 between the U.S. Department of Energy and Sandia Corporation.

BACKGROUND OF THE INVENTION

The instant invention discloses method and apparatus for calibrating sampling probes, in general, and particulate air emissions monitors, in particular, without removing the monitor from the system being monitored.

As demonstrated, in particular, by the 1990 Amendments to the Clean Air Act, air emissions of toxic, hazardous and regulated materials are coming under increasing scrutiny by the regulatory community. Furthermore, the list of regulated materials is continuing to grow. Not only will almost all air emissions sources require an operating permit but the conditions attached to those permits will become more stringent insofar as requirements for monitoring and record keeping. In addition, the Clean Air Act requires "enhanced monitoring" which has been interpreted by the Environmental Protection Agency to mandate extension of continuous monitoring to as many facilities as possible. Continuous monitoring means round-the-clock air emissions measurements to ensure continuous compliance with the emissions limitations set for that stack. Except for a few of the hazardous air pollutants, typically gaseous pollutants such as $SO_2$ and $NO_x$, continuous air emissions monitoring is not generally available. In those instances where technology is not available to perform continuous monitoring of air emissions, stack testing must be used. This technique requires that a small representative sample be removed from a larger source gas stream for analysis which is not practical at complex sources, particularly facilities that engage in "batch" operations. The inability to continuously monitor air emissions because of lack of appropriate technology requires that the facility rely on indirect mechanisms to assess their air emission of regulated hazardous materials. These typically involve some combination of process or unit operation monitors; inspection and maintenance records for process and control devices; engineering calculations based on production and operations record keeping. All very cumbersome and costly expedients and not particularly accurate.

Turning now to the specific issue of regulated metals in air emissions. In addition to the air emissions sources enumerated above, various thermal processes are often used to reduce hazardous wastes to forms that are more inert and more safely or conveniently handled. However, the offgases from such processes may still contain some hazardous compounds in either particulate or vapor form. The U.S. Environmental Protection Agency is specifically concerned about emission of various hazardous metallic compounds from thermal-waste-processing units. Because of their toxicity, the Clean Air Act lists eleven specific metals of primary concern as air toxics that require regulation: antimony, arsenic, beryllium, cadmium, chromium, cobalt, lead, mercury, manganese, nickel, and selenium. Currently, air emissions of these metals from industrial operations are measured using extractive sampling followed by off-line chemical analysis, a procedure that is costly, because of many manual operations introduces sampling errors, and typically has long turnaround times. Complete analyses of stack measurements typically are not available for two to four weeks from the time that samples are collected. Furthermore, certification tests require that more than one sample be taken for a given operating condition. The long turnaround times inherent in extractive sampling prevent the use of air emissions measurements to control operating parameters in real time. Continuous measurements of air emissions of regulated metals could ultimately provide real-time information that could be used by facility operators to modify operating parameters to improve efficiency or reduce air emissions. Furthermore, the ability to continuously measure and monitor metal emissions is useful both to assure legal compliance with various environmental regulations as well as to provide confidence to neighboring communities that health risks from such facilities are low. Measurement of hazardous metal concentrations in the off-gases is a difficult task. Although most of the metal air emissions are in the particulate phase, vapors may be significant also and must be measured simultaneously. Furthermore, the particles that contain metals may be quite inhomogeneous and particulate metals may be in any of a large number of compounds.

Any monitoring instrument designed to produce a response proportional to a parameter being monitored whether it be concentration, size, shape or any number of possible parameters of interest, must be periodically calibrated in order to determine whether the proportionality has changed during the course of operation of the instrument. This is typically accomplished by measuring the instrument response to some known standard. In the particular case of particulate emissions monitors, a stream of particles, having a known composition and/or physical properties (e.g., size) is injected into the measurement area of the monitor and its response thereto determined. Measuring the response of the particulate monitor to a known concentration of specific metals serves to calibrate the response of the instrument to those specific metals. The calibration step could be eliminated and the monitor used only for relative measurements if it were not for the fact that the response of various components of the monitor will change with time in an unknown and unpredictable way (e.g., lenses, detectors). Consequently, even using the particulate monitor in a relative measurement mode requires some form of calibration. Providing that standard samples are available, or can be prepared, and that they can be introduced into the monitoring instrument, it is generally a relatively straightforward matter to calibrate most monitoring instruments. However, in those instances where there is no ready access to the monitor (e.g., the monitor is incorporated into a larger structure such as an emissions source, or it is difficult to introduce the sample into the instrument) routine calibration may present severe problems.

SUMMARY OF THE INVENTION

The instant invention discloses method and apparatus for calibrating sampling probes, in general, and particulate air emissions monitors, in particular, without having to remove the device from the system being monitored. A source of a standard material, which can be one or more specific metals in aerosol (either solid or liquid) or vapor form, is housed in the instrument. This source, referred to hereinafter as the calibration source, can be turned on or off at will and the composition of the standard material that it emits is known (e.g., concentration or particle size of metals) and can be changed. Particularly useful calibration sources include, but are not limited to; pneumatic nebulizers, vibrating orifice aerosol generators and permeation tubes. The calibration operation is initiated by retracting a focusing lens of the sampling probe such that the focal point of the focusing lens is now within the emissions stream issuing from the calibration source. The focusing lens now collects and collimates the optical response of the standard material to a probe beam. Because the optical response is a collimated light beam it is possible to maintain optical alignment of the remaining optical components even though the focusing lens has been moved from its original position.

BRIEF DESCRIPTION OF THE DRAWINGS

The accompanying drawings, which are incorporated in and form part of the specification, illustrate the concept of the present invention and together with the description, explain an embodiment of the invention.

DETAILED DESCRIPTION OF THE INVENTION

The present invention comprises an apparatus and method for the in-place calibration of an emissions monitor.

The following introductory discussion is provided to better understand the present invention. In a particulate air emissions monitor of the type depicted in FIG. 1, a pulsed laser rapidly heats either a single particle or an assemblage of particles, in a stream to be monitored, to produce a high-temperature plasma (or "laser spark") that contains excited-state ions. As the plasma cools, ion-electron recombination occurs, and the excited-state species relax, emitting optical energy at frequencies that are characteristic of the emitting elements. FIG. 2. The spectral distribution of light emission from the plasma can be measured to identify the elemental constituents of the particles contained in the stream to be monitored and to quantify the absolute abundances of these elemental constituents. This concept has been demonstrated in the laboratory to be useful for measurements of the inorganic constituents of coal, coal char and ash particles during combustion. Elemental constituents such as Li, Na, K, Mg, Ca, Sr, Ba, Al, Ti, Mn, Fe, Si, C, H, O, and N can be identified in concentrations of several parts-per-million (ppm) of individual constituents per single particle. Other workers have shown that toxic metals, such as Hg, As, Be, Pb, and Cd can be detected in airborne particulates at the ppm level using this technique and it also has been shown that sodium can be detected in liquid aerosols at concentrations below a part per billion. The technique employed in the present invention is not limited to the analysis of toxic metals in general since other species of interest (such as alkalis or unburned carbon in flyash) can also be analyzed by measuring optical emissions at wavelengths appropriate for those species.

Continuous monitoring of air emissions of metal particles and aerosols from various sources such as incinerators, boilers and industrial furnaces, and electroplating baths has been demonstrated. This monitor can be used to monitor all eleven of the metals regulated by the Clean Air Act and has demonstrated minimum dectectable concentrations ranging from less than a part per billion for beryllium to a few hundred parts per billion for selenium and lead. A survey of permitted air emissions rates for Clean Air Act metals at Department of Energy thermal treatment facilities has shown that such diagnostic technique has sufficient sensitivity to continuously monitor for these metals.

In this description and in the appended claims the term air emission means the discharge into the air of matter which includes, but is not limited to, metallic and nonmetallic particles, individual particles or assemblages of metallic and nonmetallic particles, aerosols, and fly ash.

Figure 1:
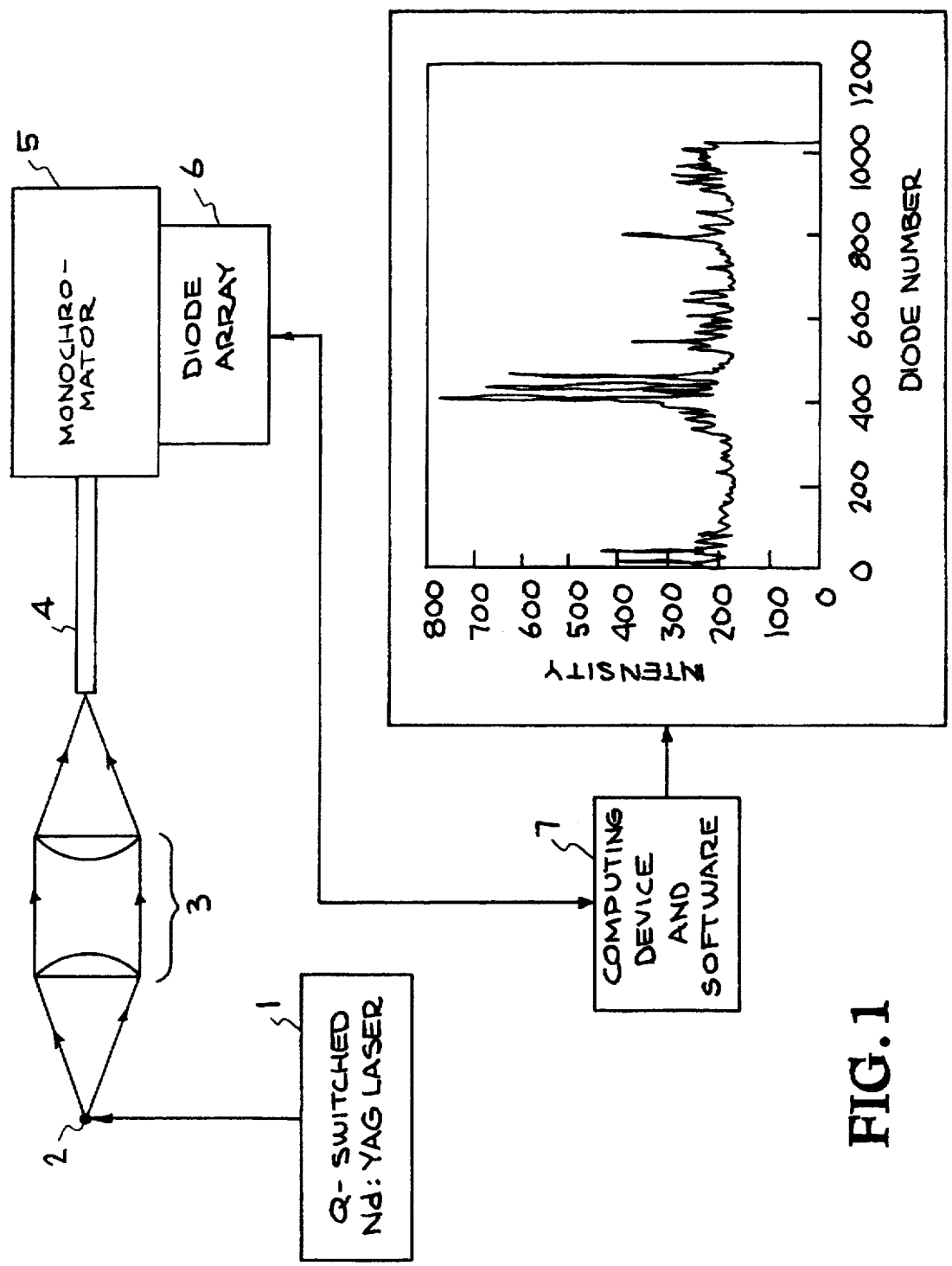
FIG. 1 is a schematic drawing which illustrates a particulate air emissions monitor.
Figure 2:
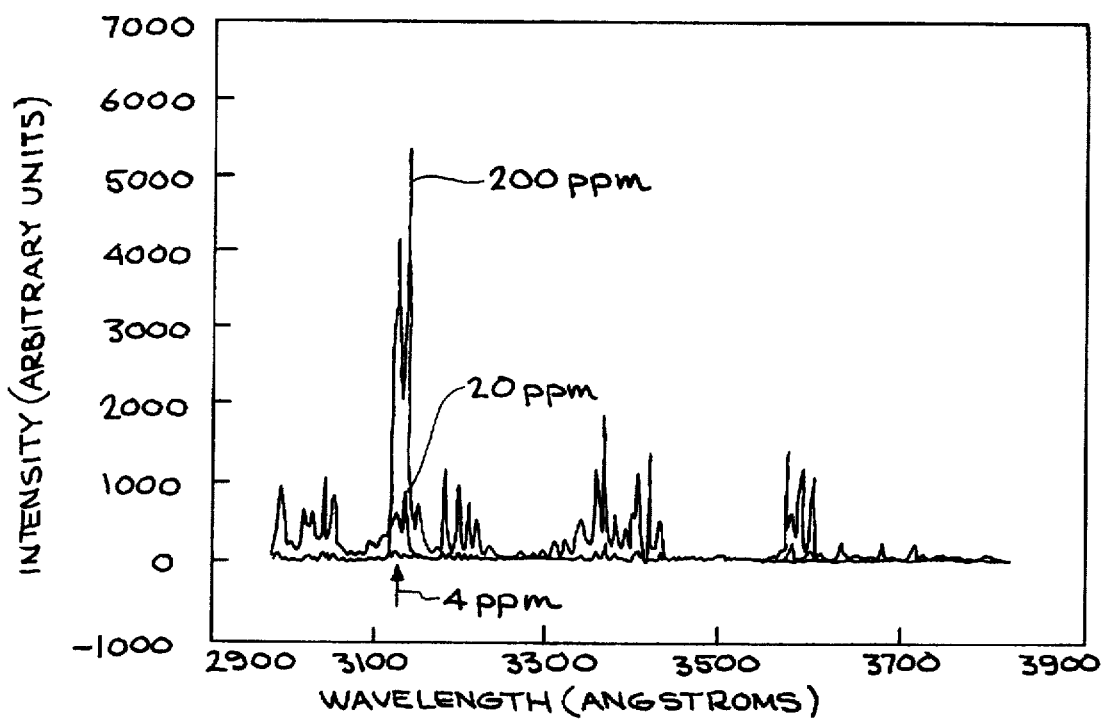
FIG. 2 shows optical emission spectra of aerosols containing respectively; 200, 20 and 4 ppm chromium (mass of chromium per unit mass of gas and aerosol).

Referring now to FIG. 1, which depicts a continuous particulate air emissions monitor M. A laser beam from a high power laser such as a Q-switched, Nd:YAG laser beam having a nominal power of 180 mJ/pulse 1, is focused into the particle flow field 2 which in this example is an aerosol. Typically, because of the high particle number density in the aerosol examined here, many particles are contained within the ellipsoidal waist region of the laser beam (roughly 200×800 μm in size) at any one time. Hence, the laser, issuing from light source 725, can be run continuously at a fixed repetition rate and an ensemble of particles is analyzed for each laser pulse. Light emitted from the plasma can be collected by a lens 3 and can be focused onto the face of a fiber-optic bundle 4, which transmits the emitted light to the entrance slit of a grating spectrometer 5 where a grating is used to disperse the emission. Depending on the desired spectral resolution, a specific grating density can be selected. Those skilled in the art will appreciate that gratings from 100 to 10,000 gr/mm can be used. The light dispersed by spectrometer 5 can be refocused onto a diode detector array 6, which measures the distribution of light intensity as a function of wavelength. The time required for plasma excitation is on the order of nanoseconds, while optical emission resulting from subsequent relaxation of excited species occurs over a period of several microseconds following plasma initiation. Because of this time-dependent nature of the optical emission, the diode array is time gated to the laser pulse using the pulse/delay generator.

Signals from the diode array are digitized by an IEEE/ DMA controller (Princeton Instruments ST116). A computer is used to control data acquisition and analysis, issuing commands over an IEEE 488 interface 7. Software can be used to access and interrogate various functional elements of the invention and determine signal intensity as a function of wavelength. In particular the capability for interactive control of data acquisition, multi-shot spectrum averaging, data display, filtering, calibration, networking, and data-file creation are provided by such. By way of example, a software such as LabVIEW® (National Instruments) can be used.

EXAMPLE 1

In this example, the particulate air emissions monitor M was used to analyze aerosols such as may be formed above a commercial chromium electroplating bath. An aerosol containing 200 micrograms chromium per standard cubic meter of air (μg/scm) was passed by the monitor. These conditions are roughly comparable to those immediately above a commercial plating bath. The chromium containing aerosol particles were in the range of 0.3 to 15 micrometers in diameter having a number density of $3 \times 10^5$ particles/cm$^3$.

Approximately 80–90% of all laser pulses induced laser breakdown of the aerosol at a laser repetition rate of 5 Hz and pulse energy of 180 mJ. FIG. 2 shows 100-shot-averaged laser-spark emission spectra obtained using a fixed spectrometer setting and a 600-gr/mm diffraction grating from which the background intensity has been subtracted. For the chromium lines in the vicinity of 312 nm, 320 nm, 336 nm, and 360 nm, both peak and integrated line intensities were proportional to the chromium concentration within 10–20% over the full range of the measurements. In order to determine the effect of potential interferences, dilute solutions of nickel and lead were added to a chromium containing aerosol. These metals were selected because they are common constituents of chromium electroplating baths. There were no significant interferences observed.

EXAMPLE 2

Figure 3:
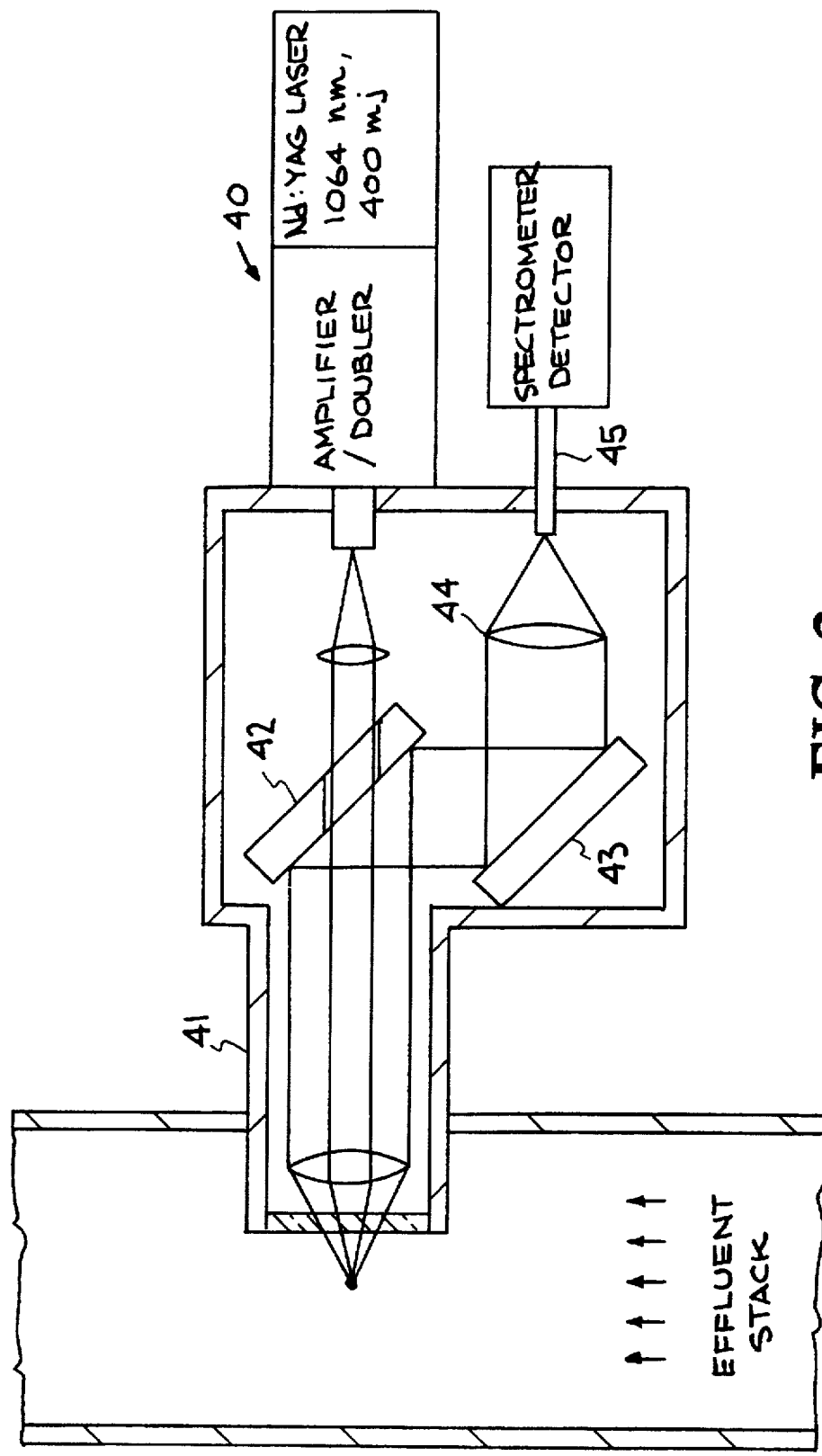
FIG. 3 illustrates an optical layout for the air emissions monitor.

This example illustrates the use of the particulate air emissions monitor M to analyze metal particles entrained in stack gases from industrial operations such as incinerators and/or boilers. Although the elements of the monitoring equipment are identical to those discussed in Example 1 above they are arranged in a different fashion relative to one another, as shown in FIG. 3. The arrangement of the optical elements shown here has special advantages. Inserting the laser light and collecting the emitted light along the same axis (i.e. coaxial) but propagating in the opposite direction permits easier access for the laser beam to particles in a confined flow geometry, as is illustrated here. Lens 41 focuses the collimated laser beam and collects and collimates the emitted light thereby reducing the number of optical elements, permitting a more compact probe than would be the case if separate lens systems were used. Furthermore, by using this lens system all the light is collimated up to lens 41 so that the measurement location, within the measurement stream being monitored, can be translated by moving only lens 41 while maintaining axial alignment between the laser focus and the source of optical emission. A small aperture in mirror 42 permits the laser beam access to the sample being analyzed without the use of a beam splitter. In this way about 90% of the collected light is reflected and a stronger signal is transmitted to the detector permitting lower concentrations to be detected. The arrangement of the optical elements shown here is for illustration only and does not describe the only configurations that may be envisioned as possible by one skilled in the art. In this embodiment, light emitted from the plasma created by the laser 40 is reflected back through a system of lenses and mirrors 41–44 to a fiber optic cable 45 which transmits the light to a spectrometer and detector for analysis.

Figure 4:
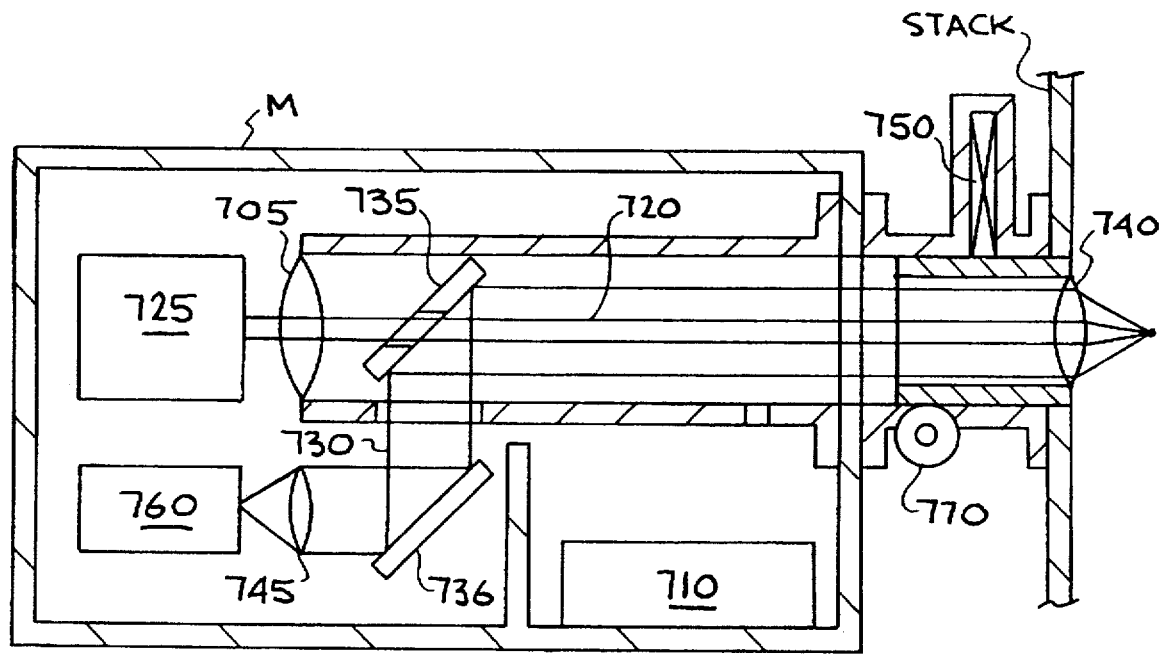
FIG. 4(a) shows an embodiment of a calibration device, according to the present invention, prior to initiation of the calibration operation.
FIG. 4(b) shows an embodiment of a calibration device with the calibration source in place and the focusing lens translated to the calibration position.
Figure 4:
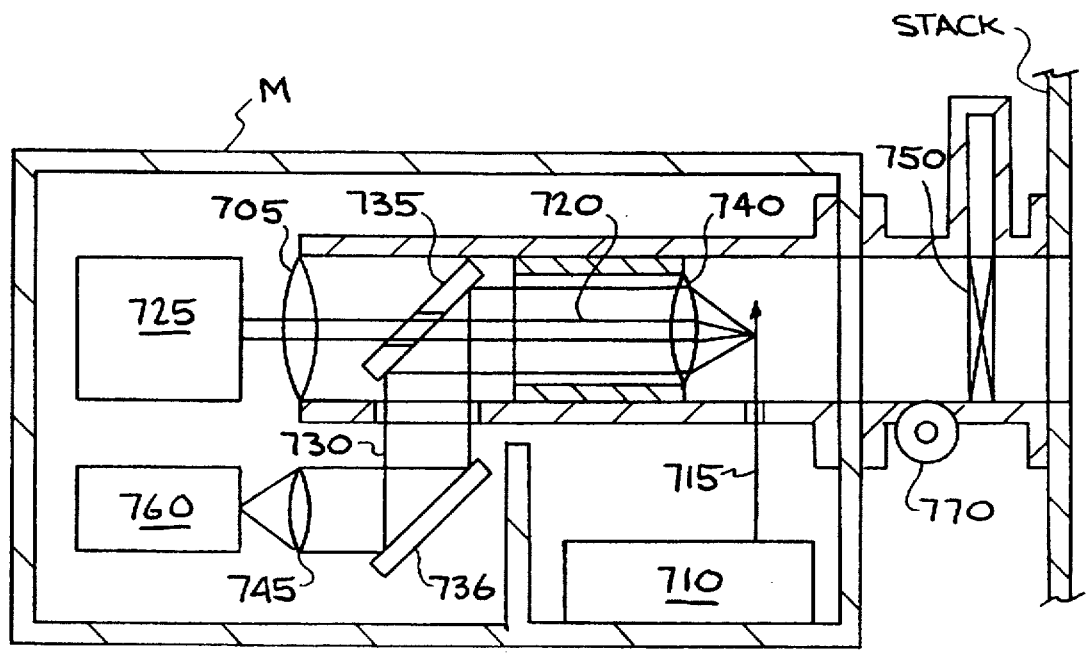

FIG. 4(a) depicts the arrangement and relationship of a calibration source 710 in a stowed position within emissions monitor M while the emissions monitor M is in the operating mode. FIG. 4(b) depicts the arrangement of the calibration source 710, while the emissions monitor M is in the calibration mode. Prior to starting the calibration operation, focusing lens 740 is axially translated from its extended position (i.e. operating position) in FIG. 4(a) to a retracted position (i.e. calibration position), depicted in FIG. 4(b) By way of example, such axial translation can be achieved by mechanical means, such as a rack and pinion gear 770, as generally depicted, or by other means, such that light beam 720 can now be focused onto a point within calibrations stream 715 issuing from calibration source 710, for analysis of the composition of emissions stream 715. Calibration source 710 contains a solution having a known chemical composition and/or physical properties (e.g., size) and is designed to eject the solution emissions stream 715 as an aerosol. Calibration source 710 can be mounted on a translation stage (not shown) in order to expose some particular point or area in emission stream 715 to focused, collimated light beam 720. In order to prevent stray emissions from the flow stream being monitored entering emissions monitor M during the calibration operation, valve 750 or similar isolating device can be used.

The optical response of the emissions monitor M in the calibration mode, FIG. 4(b) is treated in exactly the same manner as during monitoring emissions in the operating mode. Output light beam 730 from the analysis point within the calibration stream 715 issuing from calibration source 710 is collected and collimated by focusing lens 740 and is reflected from the surface of mirrors 735 and 736 onto lens 745 that focuses the output light beam onto transmitting means 760 that can be the face of a fiber optic or fiber optic bundle that transmits light to a detection means (not shown) for comparing the output light response from the emissions stream 715 issuing from calibration source 710 to the light response from the primary flow stream.

Alternatively, the surface of mirror 735 can be curved thereby serving as a focusing element. By positioning transmitting means 760 at the focal point of curved mirror 735 the collimated output beam 730 of light that originates from a point in the emissions stream can be focused directly on the transmitting means 760 thereby eliminating the need for a means to focus the return light beam (mirror 736 and lens 745) onto transmitting means 760. The detection means may be preceded by a spectrometer or other wavelength selecting device.

Following the calibration operation, the calibration signal(s) from a solution(s) having known composition(s) or physical properties is/are used to establish the response of the particulate emissions monitor to a particular element or elements in a primary flow stream or to determine if the response of the particulate emissions monitor has changed over time.

Figure 5:
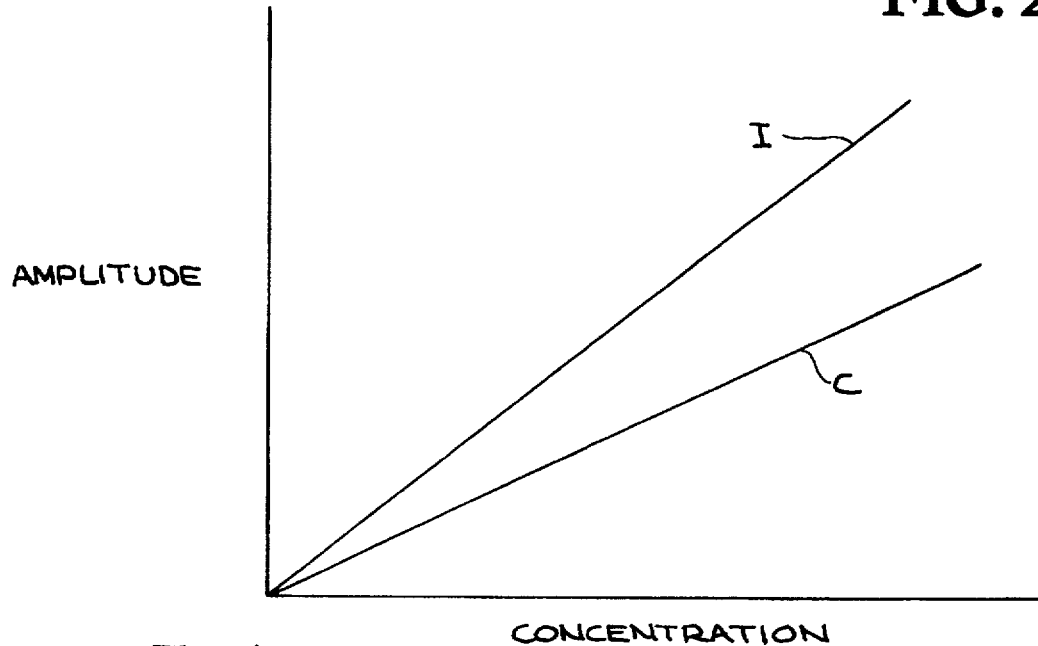
FIG. 5 depicts the relationship between amplitude and concentration of a particular species within a flow stream.

In particular and with reference to FIG. 5, the operation and calibration of the emissions monitor of the present invention will be explained in more detail. Curve I of FIG. 5 represents a relationship between the optical response of the emissions monitor, as amplitude or intensity, for a particular emission of interest (e.g. lead) and the concentration of the material in the flow stream being analyzed (e.g. in ppb). With the passage of time, the emissions monitor calibration can change such that a given optical response (amplitude) for a particular emission of interest will no longer correspond to the concentration defined by curve I. Consequently, periodic calibration of the emissions monitor described above can result in defining a new relationship between the optical response of the emissions monitor (amplitude) and concentration as depicted by curve C. Hence, variations in the optical response of the emissions monitor for a given emission of interest can be overcome by periodically calibrating the emissions monitor by analyzing an emissions stream from the calibration source having known composition. Thus, by comparing the optical response of the emissions monitor to the flow stream being monitored to the optical response of the calibration source one can accurately monitor emissions.

These foregoing examples are for illustrative purposes are should not be construed to restrict or limit the invention disclosed herein in any way. Various modifications may occur to those skilled in the art without departing from the scope of the invention as defined by the appended claims.

We claim:

1. A method of calibrating a particulate monitor, comprising the steps of:
   a.) translating a focusing lens from a position known as an operation position wherein the lens can be brought to focus on at least some particles in an environment being monitored to a position known as a calibration position whereby a calibration stream can be monitored;
   b.) introducing a calibration stream, the stream comprising particles having a known composition;
   c.) focusing an input light beam through the focusing lens onto at least some of the particles in the calibration stream;
   d.) generating an output light response
   e.) collecting and collimating the output light response thereby forming a collimated output light beam response;
   f.) separating the input light beam from the collimated output light beam response; and
   g.) comparing the collimated output light beam response from the calibration position to a collimated output light beam response from the operation position.

2. An improved apparatus for monitoring particles within a primary flow stream, wherein the improvement comprises:
   a.) a focusing lens, having a focal point, the lens for focusing a collimated input light beam from a light source onto at least some particles in the primary flow stream thereby generating a output light response;
   b.) a calibration source for emitting a calibration stream, the stream comprising particles of a known composition;
   c.) means for translating the focusing lens from an operating position as in part a.) to a calibration position as in part b.) such that the focusing lens focal point is correspondingly translated from a point within the primary flow stream to a point within the calibration stream;
   d.) means for collecting and collimating the output light response thereby forming a collimated output light beam response;
   e.) means for separating the collimated input light beam from the collimated output light beam response; and
   f.) means for comparing the collimated output light beam response when the focusing lens is in the calibration position to a collimated output light beam response when the focusing lens is in the operating position.

3. The apparatus of claim 2 wherein said calibration source is selected from a group consisting of pneumatic nebulizers, vibrating orifice aerosol generators and permeation tubes.

4. The apparatus of claim 2 wherein said means for separating the collimated input light beam from the collimated output light beam response is a mirror.

5. The apparatus of claim 4 wherein the mirror is a curved mirror having a focal point.

6. The apparatus of claim 2 wherein said light source is a laser.

7. A method of calibrating a particulate air emissions monitor, comprising the steps of:
   a.) introducing a calibration stream at a position known as a calibration position, the stream comprising particles having a known composition;
   b.) translating a focusing lens having a focal point, from a position known as an operation position wherein the lens focal point is located within a primary flow stream, the stream comprising particles having an unknown composition, to the position known as the calibration position;
   c.) focusing a collimated input light beam from a light source through the focusing lens onto at least some of the particles in the calibration stream;
   d.) generating an output light response;
   e.) collecting and collimating at least some of the output light response thereby forming a collimated output light beam response;
   f.) separating the collimated output light beam response from the collimated input light beam; and
   g.) comparing the collimated output light beam response from the calibration position to a collimated output light beam response from the operating position.

8. The method of claim 7 further including the step of isolating the particulate air emission monitor from a primary flow stream.

* * * * *